United States Patent [19]

Tomaich et al.

[11] 4,308,252
[45] Dec. 29, 1981

[54] DENTIFRICE COMPOSITION

[75] Inventors: George R. Tomaich, Greenville, S.C.; George E. Richmond, St. Louis; Noel O. Nuessle, Kansas City, both of Mo.

[73] Assignee: Young Dental Mfg. Co., St. Louis, Mo.

[21] Appl. No.: 90,025

[22] Filed: Oct. 31, 1979

[51] Int. Cl.³ .................. A61K 7/16; A61K 7/18; A61K 33/16
[52] U.S. Cl. .................. 424/52; 424/151; 424/49
[58] Field of Search .................. 424/49-58

[56] References Cited

U.S. PATENT DOCUMENTS

| | | | |
|---|---|---|---|
| 1,262,888 | 4/1918 | Westlake | 424/55 |
| 1,411,681 | 4/1922 | Burlew | 424/49 |
| 2,778,045 | 1/1957 | Bly et al. | 424/49 |
| 3,151,028 | 9/1964 | Hay et al. | 424/55 |
| 3,228,845 | 1/1966 | Najjar | 424/49 |
| 3,431,339 | 3/1969 | Gyarmathy et al. | 424/52 |
| 3,892,843 | 7/1975 | Muhler et al. | 424/52 |
| 3,932,606 | 1/1976 | Barth et al. | 424/52 |
| 4,157,386 | 6/1979 | La Rochelle | 424/52 |
| 4,165,366 | 8/1979 | Mellberg | 424/49 |
| 4,165,368 | 8/1979 | Gaffar | 424/52 |

FOREIGN PATENT DOCUMENTS 2816513  10/1978  Fed. Rep. of Germany ........ 424/49

*Primary Examiner*—Shep K. Rose
*Attorney, Agent, or Firm*—Rogers, Eilers & Howell

[57] ABSTRACT

A dental prophylaxis tablet is disclosed containing abrasives and anticaries compounds. The tablet is hard enough to withstand normal storage and handling. The tablet also contains dispersing and wetting agents so that it may be readily constituted into a dental prophylaxis paste by the addition of water and may contain sweeteners and flavors. A typical tablet is approximately one gram in weight and has hardness of about 3.5 to 4.0 kilograms (Pfizer tester). A typical tablet can be hydrated in approximately 60 seconds with the addition of water to form a prophylaxis paste.

A typical formulation is: feldspar 61%, Cabosil (TM) 1%, Instant ClearJel (TM) 5%, Sta $R_x$ 1500 (TM) 25%, sodium saccharin 0.5%, sodium citrate 0.5%, stannous fluoride 5%, Stearowet-C (TM) 0.5% and flavors 1%.

10 Claims, No Drawings

DENTIFRICE COMPOSITION

BACKGROUND AND SUMMARY OF THE INVENTION

The use of fluoride chemicals in compositions for dental hygiene, such as mouth washes, tooth paste for daily care and dental prophylaxis cleaning compounds, has been known for some time. The known treatments include the use of soluble fluorides, such as sodium fluoride, and also the use of compounds containing stannous ion, such as stannous fluoride. Other sources of both stannous ions and fluoride ions have been used in various combinations, for example as combinations of stannous chloride and sodium fluoride. An abrasive material is also normally included in dentifrice compounds. The abrasive may be various insoluble phosphates, silicates, pumice flour, feldspar, zirconium silicate, silicon dioxide, or other abrasive materials, which if chosen with the proper particle size, are capable of cleaning and/or polishing the surfaces of teeth, without damaging the tooth structure.

It has also been known that there is a gradual loss of strength and anticaries effectiveness of stannous ions and fluoride ions in dentifrices, due to reactions which occur over time in the tooth paste or dental prophylaxis composition. For example, the stannous ions in an aqueous medium, such as tooth paste, may be gradually hydrolysed to stannic oxide or other stannic compounds which are insoluble and ineffective as anticaries agents. In addition, other complexes and insoluble compounds may be formed over time due to reactions which occur in the toothpaste medium so that the strength of the stannous ion may be considerably reduced prior to use of the tooth paste or dental prophylaxis paste.

Similarly, there is a loss of strength of the fluoride ion over time, particularly in an aqueous medium, due to the formation of insoluble reaction products with other chemicals which may be present in the medium. For example, the fluoride may react with a free calcium ion to form insoluble calcium fluoride, which is not effective as an anticaries agent. In addition, the fluoride may react with some humectants, such as glycerine, to form insoluble compounds which are not effective anticaries agents.

The art has taken numerous measures to compensate for or to minimize the reduction of strength of the anticaries agents over time. The art has tried to provide abrasives which are not contaminated by soluble calcium, for example, by attempting to procure and use abrasives, such as silicon dioxide or pumice, which are chosen to contain minimum amounts of available calcium. The art has also attempted to manufacture highly insoluble abrasives such as insoluble forms of calcium phosphate. These measures have been only partially effective. Over time, even insoluble forms of calcium phosphate release soluble calcium in sufficient quantity to react with fluoride. It is also extremely difficult to procure natural abrasives, such as silicon dioxide or pumice, which have a calcium content which is uniformly and acceptably low.

Another method of compensating for reduction of strength in dentrifrices containing anticaries agents has been to increase the content of those agents to a level considerably above their therapeutic optimum, realizing that the strength of these materials will be reduced over time. Enough of these materials are placed in the composition as a "safety factor" that even after some time the strength will remain at an acceptably high level.

Compensating for loss of strength by adding an incremental "safety factor" above the optimum level has created some problems, however, particularly in dental prophylaxis compositions. "Safety factor" quantities add a bad taste and may cause nausea and vomiting in some patients. This may be particularly true in combination with some abrasives, with which the effect may be quite pronounced.

With dental prophylaxis compositions, the art has used another tactic for minimizing the effect of time on the strength of the anticaries agents. The materials forming the dental prophylaxis dentifrice are supplied in two parts. One part is a dry powder containing the abrasive and ancillary compounds. The second part is a solution of the anticaries compound, for example an aqueous solution of stannous fluoride. The two parts are mixed just prior to use. This minimizes the reaction between the anticaries material and the abrasive, but does not eliminate the hydrolysis of stannous ions. Oxidation, formation of insoluble tin compounds and other reactions to reduce the strength of the anticaries compound can proceed. Moreover, this technique introduces a problem in handling, since it is necessary to measure the abrasive and the solution and then mix to form a paste. This is inconvenient, requires time, and may introduce errors in measurement and failure of complete mixing of the ingredients. Separation may occur in the solid ingredients over time, in the powder form, which affects the composition of the paste.

Applicant is aware of the following U.S. patents:
U.S. Pat. No. 2,876,168,
U.S. Pat. No. 3,105,013,
U.S. Pat. No. 3,105,798,
U.S. Pat. No. 3,151,027,
U.S. Pat. No. 3,257,282,
U.S. Pat. No. 3,282,792,
U.S. Pat. No. 3,330,732,
U.S. Pat. No. 3,378,445,
U.S. Pat. No. 3,445,567,
U.S. Pat. No. 3,756,386,
U.S. Pat. No. 3,804,946,
U.S. Pat. No. 3,892,843,
U.S. Pat. No. 4,016,255 and United Kingdom Pat. No. 845,611. The disclosures of the above patents are incorporated by reference herein.

Applicant has discovered a dentifrice composition that does not lose any substantial strength in its anticaries activity over time. In particular, applicant has provided a dentifrice composition that does not lose strength of stannous and fluoride ions due to reaction with time to form insoluble and unavailable compounds. Applicant's composition does not require a great excess of anticaries material and in particular does not require a great excess of stannous and fluoride ions to maintain a therapeutic level of the anticaries material over time.

Applicant's composition can maintain an effective level of anticaries material, such as stannous and fluoride ions, over time without requiring such a high initial level of these anticaries materials that the product has an unacceptably bad taste or causes unacceptable incidence of nauseous sickness or vomiting in patients on which the material is used.

Applicant's dentifrice can be supplied as a one component mixture in which all therapeutic and ancilliary ingredients are premixed and combined in dosage form and at dosage levels. Applicant's material does not require measuring and mixing of the therapeutic ingredients at or just before the use of the dentifrice. Applicant's composition does not require precise selection of abrasives, but can use any acceptable dental abrasive, cleaner or polisher without having extremely narrow tolerances for pure or highly insoluble material. Applicant's dentifrice can tolerate reasonable levels of soluble calcium without reduction in efficacy of the professional prophylaxis paste produced therefrom. Applicant's dentifrice can use any soluble dental therapeutic fluoride without extreme regard for taste of the same, since the material is not used in greatly excessive amounts, and can use any readily soluble dental stannous ion source without great regard to taste, since that also is not used in excessive amounts. The anticaries reagents used in the prophylaxis paste produced in the applicant's product are used at or near the optimum levels without any substantial loss of strength over time. The dental prophylaxis paste produced from applicant's dentifrice has excellent rheological properties for working with a standard dental prophylaxis cup.

Applicant's dental prophylaxis paste does not require that the therapeutic ingredients be mixed shortly prior to use. Substantially all of the preparation can be done long prior to use of the dentifrice. The dosage level is not subject to the errors of individual mixing and remains substantially uniform from one dosage unit to the next.

Applicant has provided a dental prophylaxis precursor or pellet which is readily hydratable with the addition of water to rapidly form a dental prophylaxis paste having abrasive and anticaries compounds and all necessary or desired ancilliary compounds such as flavorings, wetting agents and other materials.

DESCRIPTION OF THE PREFERRED EMBODIMENTS

In general applicant's dentifrice composition will contain an anticaries material, at or slightly above the optimum therapeutic level, combined with suitable abrasives, dispersants, buffers, mold release compounds and sweeteners or flavors as needed or desired. (It will be appreciated that less than the optimum therapeutic amounts may be used, with a corresponding reduction in efficacy of the resulting paste or that greater than optimum levels may be used.) The compounds are mixed in their dry form and pelleted to a suitable hardness so that the composition will maintain its dosage level and structural integrity throughout transportation, distribution and handling. Of special value as anticaries agents are sources of stannous and fluoride ions, including but not limited to stannous fluoride, sodium fluoride, stannous zirconium hexafluoride, stannous chlorofluoride, stannous chloride and mixtures thereof. The abrasive may be any acceptable dental abrasive and cleaning and polishing agents, including, but not limited to feldspar, zirconium silicate, silicon dioxide, pumice flour, insoluble phosphates and mixtures thereof. Particularly useful to the composition are stannous fluoride as an anticaries agent and feldspar as an abrasive material.

Various dispersing and suspending agents may be used, such as gums, cellulosic gums or colloidal silicas. Sodium lauryl sulfate and other suitable detergent materials may be used as wetting agents. Mold release compounds, for example calcium stearate or other insoluble soaps, may be used. Buffers, such as sodium citrate and other suitable buffers, may be used to maintain the dental paste formed from the composition at a suitable pH. The use of buffers is not essential, but may be useful in some compositions. Various sweeteners, such as sodium saccharin, and flavors, such as oil of sassafras, and other common flavorings and sweetening agents may be used.

Typically the compositions are mixed in dry form to form a uniformly dispersed powdered mixture and then tableted on a tableting machine, of a type known in the art, to a suitable hardness. The tablets may be of any convenient type. Tablets of ½–2 grams each are satisfactory to prepare paste for treating one patient. One or more tablets may be used per patient, as required. Hardnesses in the range of about 3 to 8 kilograms crushing strength are satisfactory. It will be appreciated that the hardness (strength) of the tablets must be effective to maintain the structural integrity of the tablets throughout production, packaging, handling, transportation, storage and use to maintain the dosage and tablet size constant. In addition the tablet must be hydratable and must retain the ability to hydrate throughout the above conditions.

The dentifrice composition may contain abrasives above about 50% by weight, for example, from about 50% to 70%, though more may be used if desired. Dispersing agents in a range of about 1% to 10%; wetting agents of about 0.005% to 0.5%; sweeteners of about 0.05% to 5.0%; buffers of about 0.5% to 5.0%; therapeutic anticaries agents of about 2% to 10%; mold release agents of about 0.05% to 2.0% and flavors from about 0% to 5.0% provide a workable and effective formulation. All percentages are given as percent by weight.

The therapeutic anticaries agent may be added in quantities over a wide range of levels. It will be appreciated, however, that it is not normally necessary to add the dental therapeutic agents at a level much greater than their optimum therapeutic concentration, since they do not decrease substantially in strength over time in the dry composition. The accepted preferred quantity for stannous fluoride, particularly in the United States, is about 5%, providing stannous ion of about 3.75% and about 1.25% fluoride. Normally the source of the anticaries agents, of whatever source material, will be chosen to supply about this quantity of stannous and fluoride ions or not substantially greater than this quantity of stannous and fluoride ions. Greater or lesser amounts may be used, if desired. In some instances, where no anticaries agents are desired at all, they may be eliminated. The cleaning value, ease of preparation, storage, transportation and hydration of course remain. For daily topical use, where anticaries activity is desired, the dosage of the anticaries agents will of course be lower than for professional or periodic use. Normally a topical preparation would contain about 0.2% to about 1% by weight of stannous fluoride.

The tablet will readily hydrate with addition of water, within about one minute. An equal amount of water, by weight, is normally used to hydrate the tablets. About one cubic centimeter of water will hydrate one gram of tablet weight. The proportion of water to tablet may be varied, as desired by the user, to vary the consistency of the paste.

The following example illustrates a formulation and procedure for preparing applicant's dental prophylaxis tablet.

EXAMPLE I

A dental prophylaxis tablet of the invention was formulated from:

| | |
|---|---|
| feldspar (40–325 Mesh) | 61.5% |
| Cabosil TM colloidal silica | 1.0% |
| Instant ClearJel TM National Starch Co. | 5.0% |
| Sta R$_x$ 1500 TM Color Con Corp. | 25.0% |
| sodium saccharin | 0.5% |
| sodium citrate | 0.5% |
| stannous fluoride | 5.0% |
| Stearowet-C TM mold release and wetting agent containing 90% calcium stearate and 10% sodium lauryl sulfate | 0.5% |
| flavor | 1.0% |

Enough ingredients were prepared to manufacture 500 grams of mix. The feldspar and colloidal silica were mixed using a horizontal ribbon dry blender. The Instant ClearJel, Cabosil and Sta R$_x$ 1500 were added to the first mixture in the mixer and blended to form a uniform mixture. The sodium saccharin, sodium citrate and stannous fluoride were then added to the mixture. Mixing was continued until a uniform dry mix was achieved. The Stearowet-C was then added and blended until uniformly mixed. The flavor was added as a last step and mixed until thoroughly dispersed.

The mix was removed from the mixer and passed through a tableting die on a Model 204 Colton TM tableting press, operated at near the maximum pressure. The tablets from the die were then passed over a 16 mesh screen and retableted through the die. The die was a standard 7/16 inch concave die. Tablets weighing approximately 700 mg and having a hardness of between about 3.5 and 4.0 kg. (using a Pfizer tester) were produced. The tablets hydrated with an equal weight of tap water within 60 seconds to form a paste having only a soft dry core. The core readily broke up and dispersed in the paste when manipulated with a dental prophylaxis cup.

The tablets formed from the example above were subjected to stability tests to determine the change in strength of the therapeutic agents with time. The tablets were stored in enclosed plastic bottles and analyzed at intervals to determine the change in strength. Storage was at 37° C. for the first six months of testing and at room temperature thereafter. Table I records the results of those tests.

TABLE I

| | Material | |
|---|---|---|
| Theoretical content of therapeutic Agent | Example I 5% Stannous Fluoride (Fluoride content assay) | Example I 5% Stannous Fluoride (Stannous content assay) |
| Initial Assay | 5.25% (1.05% th) | 4.86% (97.2% th) |
| 1 month | 5.09% (101.8% th) | 4.99% (99.8% th) |
| 2 month | 5.05% (101.0% th) | 4.72% (94.4% th) |
| 3 month | 4.68% (93.6% th) | 4.84% (96.8% th) |
| 4 month | 5.03% (100.6% th) | 4.84% (96.8% th) |
| 5 month | 4.89% (97.8% th) | 4.65% (93% th) |
| 6 month | 4.81% (96.2% th) | 4.47% (89.4% th) |
| 15 month | 5.3% | 4.47% |

TABLE I-continued

| | Material | |
|---|---|---|
| Theoretical content of therapeutic Agent | Example I 5% Stannous Fluoride (Fluoride content assay) | Example I 5% Stannous Fluoride (Stannous content assay) |
| | (106% th) | (89.4% th) |

The dental prophylaxis materials of Example I was tested by use in cleaning teeth by a trained hygienist. The tablets were rehydrated by addition of about equal amount of water and used using a standard prophylaxis cup and handpiece. All of above materials rehydrated readily to form a viscous paste which did not exhibit excessive slinging in the mouth of the patient or onto the dental handpiece. The paste cleaned the teeth and left a high polish on the teeth surfaces. All were judged to be satisfactory dental therapeutic compositions.

While the invention has been described with reference to the above examples, it should be understood that various changes, modifications, and alterations may be made in the material utilized. The proportions of such materials, the manner of formulating applicant's dentifrice material and the resulting dentifrice composition may be varied without departing from the spirit and scope of the invention as defined in the appended claims.

What is claimed is:

1. A dosage stable professional prophylaxis paste precursor tablet which is readily hydratable on addition of water to form a professional anticaries prophylaxis paste, the tablet having an effective amount of a dental cleaning and polishing abrasive and an effective amount of a dental anticaries material in a premeasured dosage unit, the tablet being substantially dosage stable on storage and being compacted to a hardness effective to remain intact in normal storage and transportation, the tablet containing an effective amount of wetting and dispersing agents to be readily hydratable on addition of about an equal amount of water, to form a premeasured unit for use as a professional anticaries dental prophylaxis paste.

2. A dosage stable professional dental prophylaxis paste precursor tablet which is readily hydratable on addition of water to form a professional anticaries prophylaxis paste, the tablet containing between about 50 to 70 percent by weight of a dental cleaning and polishing abrasive selected from the group consisting of feldspar, zirconium silicate, silicon dioxide, pumice, dental abrasive phosphates, and mixtures thereof, the tablet containing between about 2 and 10 percent by weight of an anticaries agent selected from the group consisting of stannous fluoride, sodium fluoride, stannous zirconium hexafluoride, stannous chloro-fluoride, stannous chloride and mixtures thereof and sufficient to supply fluoride ions and stannous ions in therapeutically accepted amounts, the tablet containing between 1 percent and 10 percent by weight of a dispersing agent selected from the group consisting of gums, cellulosic gums, colloidal silicas and mixtures thereof, the tablet containing between 0.05 percent to 5 percent by weight sweetener, between about 0.05 to 2 percent by weight of a mold release compound and between about 0 to 5 percent by weight flavor, the tablet having a crushing hardness of between about 3 to 8 kilograms and being readily hydratable within about 60 seconds on addition of about an equal weight of water to form a professional anticaries dental prophylaxis paste.

3. The tablet of claim 2 wherein the tablet is between about one-half to two grams and contains feldspar of a particle size of between about 40 to 325 mesh, in a proportion of about 60 percent by weight, and wherein the tablet contains colloidal silica at about 1 percent, additional thickeners in the level of about 30 percent, saccharin sweetener of about ½ percent, about ½ percent of a sodium citrate buffer, about 5 percent stannous fluoride of a solubility and in proportions sufficient to provide about 3.75 percent stannous ion and about 1.25 percent fluoride ion on hydration, and wherein the tablet contains about 0.5 percent mold release compound and flavoring compounds of about 1 percent by weight, the tablets substantially retaining the stability of the therapeutic stannous fluoride ingredients for at least about 15 months.

4. In a method of professionally cleaning teeth by a dental prophylaxis treatment using a dental prophylaxis cup and a professional dental prophylaxis paste, the improvement comprising forming a dental prophylaxis paste in situ by hydrating a dosage stable, dry, hard and compact tablet to form a professional dental prophylaxis paste, cleaning teeth using a dental handpiece and dental prophylaxis cup and using the hydrated paste, the tablet hydrating to a paste on addition of about an equal weight of water to form the dental professional paste, the tablet containing an effective amount of a professional dental cleaning abrasive and an effective amount of an anticaries material, the hydrated paste formed from the tablet exhibiting satisfactory rheological properties, in not slinging excessively, when worked with the dental prophylaxis cup, and the tablet retaining the strength of the anticaries material during storage under dry condition and remaining substantially intact under normal storage and handling.

5. The method of claim 4 wherein the tablet hydrates to a paste within about 60 seconds.

6. The method of claim 4 wherein the tablet contains between about 2 to 10 percent by weight of an anticaries agent selected from the group consisting of stannous fluoride, sodium fluoride, stannous zirconium hexafluoride, and stannous chloro-fluoride, stannous chloride, and mixtures thereof, sufficient to supply fluoride and stannous ions in therapeutically acceptable amounts, the tablet containing between about 50 to 70 percent by weight of a dental cleaning and polishing abrasive selected from a group consisting of feldspar, zirconium silicate, silicon dioxide, pumice, dental abrasive phosphates, and mixtures thereof, between about 1 to 10 percent by weight of a dispersing agent selected from the group consisting of gums, cellulosic gums, colloidal silicas and mixtures thereof, the tablet containing between 0 to 5 percent of a pH buffer, between about 0.05 to 5 percent by weight sweetener, between about 0.05 to 2 percent by weight of a mold release compound and between about 0 to 5 percent by weight flavor, the tablet having a crushing hardness of between about 3 to 8 kilograms and being readily hydratable within about 60 seconds on addition of about an equal weight of water to form a professional dental anticaries prophylaxis paste.

7. The tablet of claim 1 wherein the tablet contains between about 50% to 70% by weight of a dental cleaning and polishing abrasive.

8. The tablet of claim 1 wherein the tablet contains between about 2% to 10% by weight of anticaries material.

9. The tablet of claim 1 wherein the anticaries agents are selected from the group consisting of stannous fluoride, sodium fluoride, stannous zirconium hexafluoride, stannous chloro-fluoride, stannous chloride and mixtures thereof.

10. The tablet of claim 1 wherein the tablet contains wetting and dispersing agents selected from the group consisting of gums, cellulosic gums, colloidal silicas, detergents and mixtures thereof.

* * * * *